United States Patent [19]

Fujita et al.

[11] 4,270,003
[45] May 26, 1981

[54] HYDROQUINONE DERIVATIVES AND PREPARATION THEREOF

[75] Inventors: Yoshiji Fujita; Takashi Ohnishi; Takashi Nishida, all of Kurashiki, Japan

[73] Assignee: Kuraray Co., Ltd., Kurashiki, Japan

[21] Appl. No.: 62,031

[22] Filed: Jul. 30, 1979

[30] Foreign Application Priority Data

Aug. 2, 1978 [JP] Japan ................................. 53-94727
May 8, 1979 [JP] Japan ................................. 54-56677

[51] Int. Cl.³ .................... C07C 147/08; C07C 43/20; C07C 43/205
[52] U.S. Cl. .................................. 568/33; 568/608; 568/609
[58] Field of Search .................... 260/607 AR; 568/33

[56] References Cited

U.S. PATENT DOCUMENTS

4,089,873  5/1978  Rapoport et al. ............... 260/396 K

FOREIGN PATENT DOCUMENTS

2746398  4/1978  Fed. Rep. of Germany .
1396622  6/1975  United Kingdom .

Primary Examiner—Glennon H. Hollrah
Assistant Examiner—M. C. Eakin
Attorney, Agent, or Firm—Burns, Doane, Swecker & Mathis

[57] ABSTRACT

The novel hydroquinone derivatives of the formula (I) are useful intermediates for the preparation of coenzyme Q, vitamin K and the polyprenyltrimethylquinones:

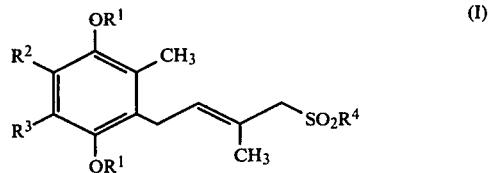

wherein $R^1$ is lower alkyl, lower alkoxy lower alkyl or methoxyethoxymethyl, $R^2$ and $R^3$ are each methyl or methoxy, or $R^2$ and $R^3$, taken together with the carbon atoms from which they depend, define a benzene ring, and $R^4$ is a substituted or unsubstituted aromatic hydrocarbon. The compounds (I) are readily prepared either by reacting a Grignard reagent of the formula (II) with a halosulfone (III) in the presence of a copper compound, or by reacting a copper derivative (II') of the Grignard reagent (II) with a halo-sulfone (III), as follows:

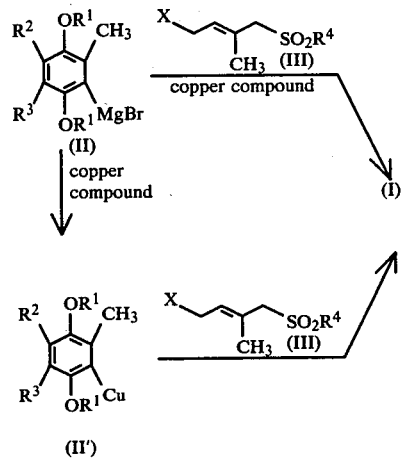

wherein $R^1$, $R^2$, $R^3$ and $R^4$ are defined as above, and X is a halogen atom or a tosyl group.

15 Claims, No Drawings

HYDROQUINONE DERIVATIVES AND PREPARATION THEREOF

BACKGROUND OF THE INVENTION

1. Field of the Invention

The present invention relates to novel hydroquinone derivatives useful as intermdiates in the synthesis of coenzyme Q, vitamin K and the polyprenyl-trimethyl-quinones and to a novel process for the preparation of such derivatives.

2. Description of the Prior Art

Quinones having polyprenyl side chains, such as vitamin K and coenzyme Q, and reflecting the following structural formulae, are important medicinal chemicals:

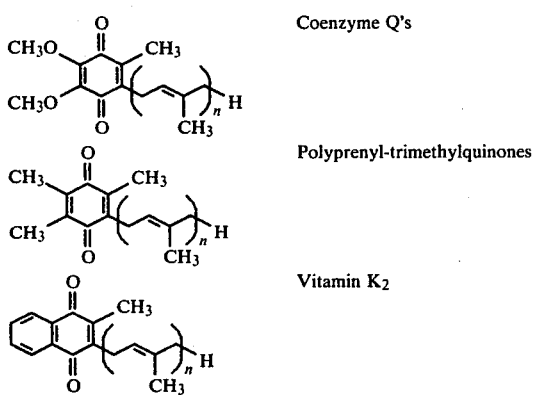

wherein n represents the number of isoprene units.

The compounds of the aforenoted structural formulae wherein n is 1-12 are known [cf., e.g., R. H. Thomson, *Naturally Occurring Quinones*, second edition, Academic Press (1971) and *Helvetica Chimica Acta*, 46, 2517 (1963)]. These compounds may, depending upon the number of the isoprene units, exhibit different pharmacological activities. In this respect, and insofar as the stereochemistry of the double bonds in the polyisoprene chain is concerned, an all-trans geometry is considered the more desirable.

A process has been known for a relatively long period of time for the synthesis of such quinones, which process comprises, utilizing the synthesis of coenzyme Q as an example, reacting 2,3-dimethoxy-5-methyl-hydroquinone (aromatic nucleus) with a prenyl alcohol or derivative thereof and oxidizing the resultant condensation product to the corresponding quinone [see, e.g., British Patent Specification No. 928,161; *Chemical Abstracts*, 74, 125168 v, (1971)].

The above process is illustrated by the following reaction sequence:

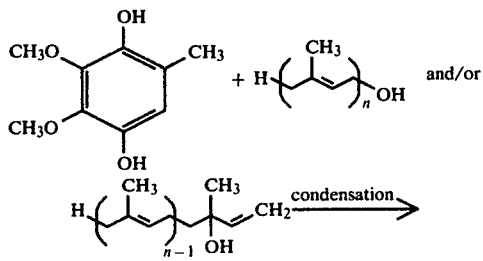

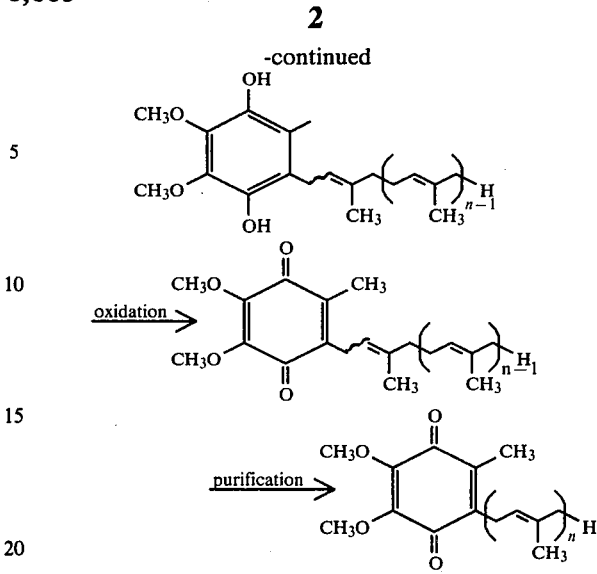

The above condensation may be carried out in the presence of an acid catalyst, such as formic acid, sulfuric acid, hydrochloric acid, phosphoric acid, p-toluenesulfonic acid or another protic acid, or zinc chloride, aluminum chloride, boron trifluoride etherate or another Lewis acid. However, said reaction is accompanied by such side reactions as cyclization within the polyprenyl side chain and chromanol cyclization of the condensation product, and as a result the yield of the desired compounds is at most 30%. To avoid this disadvantage, there have been proposed, for example, (i) a method which comprises reacting a 2,3-dimethoxy-5-methylhydroquinone dimethoxymethylether-6-magnesium halide as the aromatic nucleus-forming substance with a $\pi$-allylic nickel complex of a polyprenyl halide, (ii) a method which comprises reacting said aromatic nucleus-forming substance with a polyprenyl halide in the presence of palladium chloride or dichlorobis(triphenyl-phosphine) nickel as catalyst [*Chemical Abstracts*, 84, 179876z and 179877a (1976)], (iii) a method which comprises reacting a 2,3-dimethoxy-5-methyl-6-halo-hydroquinone diacetate (aromatic nucleus-forming substance) with a $\pi$-allylic nickel complex of a polyprenyl halide [British Patent Specifications Nos. 1,424,004 and 1,426,769], and (iv) a method which comprises reacting 2,3-dimethoxy-5-methylhydroquinone borate ester with a prenyl alcohol or derivative thereof [British Patent Specification No. 1,529,326 and U.S. Pat. No. 4,061,660].

While the reaction yield can indeed be improved to some extent by the immediately aforesaid methods, the stereo-selectivity, which is another important problem in obtaining all-trans isomers, is not at all improved. For example, in the event that solanesol, which is an all-trans $C_{45}$ polyprenyl alcohol and obtainable by extraction, e.g., from natural tobacco leaf or potato leaf, is subjected to chain extension to $C_{50}$ and then to condensation with an aromatic nucleus, a mixture of stereoisomers is obtained in which the cis/trans ratio is typically between about 3/7 to 2/8. The purification procedure for recovering the trans isomer from said mixture is, however, very complicated and, moreover, the structural components (i.e., the side chain and aromatic nucleus) constituting the separated cis isomer are completely lost. Accordingly, a serious need exists in this art to overcome all of the aforenoted disadvantages.

SUMMARY OF THE INVENTION

It has now surprisingly been found that those disadvantages which heretofore have plagued this art are readily obviated by first introducing a trans $C_5$-prenyl group into the aromatic nucleus of suitable hydroquinone starting material, to provide the novel compounds having the structural formula (I):

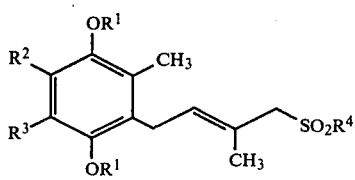

wherein $R^1$ is lower alkyl, lower alkoxy lower alkyl or methoxyethoxymethyl, $R^2$ and $R^3$ are each methyl or methoxy, or $R^2$ and $R^3$, taken together with the carbon atoms from which they depend, form a benzene ring, and $R^4$ is a substituted or unsubstituted aromatic hydrocarbon residue.

The prenyl moiety of the compounds (I) is next chain extended by polyprenylation with a reactant having one less isoprene unit, or five less carbon atoms, than the ultimate desired number of recurring prenyl units in such side chain, and such that the total number of recurring prenyl units in the side chain of the desired final product is provided by the sum of the prenyl moiety comprising the compounds (I) and those prenyl moieties comprising the polyprenylation chain extending reactant.

Moreover, the foregoing seriatim technique has been found to be markedly more attractive, both from a yield point of view, as well as from a stereoselectivity standpoint, than those known processes above described which feature reacting a prenyl alcohol derivative, e.g., solanesyl halide or decaprenyl halide, with the hydroquinone starting material, to directly obtain the desired final product.

The subject compounds (I) are eminently well suited as intermediates for carrying out the process of the invention. Moreover, the preparation thereof can be accomplished quite easily and inexpensively.

Accordingly, the compounds (I) of the present invention are useful as intermediates for the production of coenzyme Q, vitamin K and other polyprenyltrimethylquinones by reaction with a polyprenyl halide having any desired chain length.

DETAILED DESCRIPTION OF THE INVENTION

More particularly in accordance with this invention, the compounds (I) are prepared by reacting a compound having the following structural formula (II):

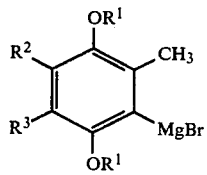

wherein $R^1$, $R^2$ and $R^3$ are as defined in formula (I), with a compound having the following structural formula (III)

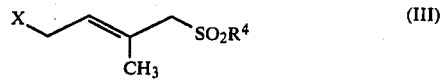

wherein $R^4$ is defined as in formula (I) and X is a halogen atom (e.g., chlorine or bromine atom) or a tosyl group, with the aid of a copper compound.

The compounds of formula (III) can be prepared by reacting the corresponding sulfonyl halide with isoprene in the presence of a cuprous halide [*J. Org. Chem.*, 35, 4217 (1970)].

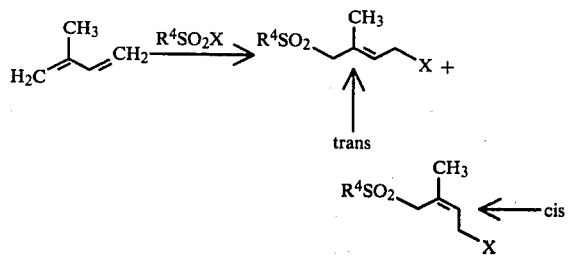

In the above equation, $R^4$ and X are as defined above.

The advantages of the above reaction are that the starting materials, isoprene and sulfonyl halide, are inexpensive, that the reaction yield is high, and that the resulting trans isomer can easily be separated from the cis isomer. Therefore, the reaction is very economical, wven when the separated cis isomer is discarded. Generally, the trans isomer (solid) can be separated from the cis isomer (liquid) by utilizing their melting point differences. The substituted or unsubstituted aromatic hydrocarbon residue represented by $R^4$ in formula (III) is a group inert to Grignard reagents, such as phenyl, tolyl, xylyl, napthyl, and the like.

The Grignard reagent of formula (II), which is a starting material in practicing the invention, is produced by reacting magnesium with the corresponding bromide under conditions known per se (e.g., in tetrahydrofuran, at a temperature of 0°–60° C.). The reaction of the thus prepared Grignard reagent of formula (II) with the halo-sulfone of formula (III) with the aid of a copper compound includes, within the scope of the present invention, (A) the reaction of Grignard reagent (II) with halo-sulfone (III) in the presence of the copper compound, for example, the reaction effected by adding Grignard reagent (II) to a solution of a mixture of compound (III) and the copper compound, and (B) the reaction of the copper derivative of the Grignard reagent (II), having the following structural formula (II′), with compound (III), for example, the reaction effected by mixing Grignard reagent (II) with the copper compound and adding the resulting reaction mixture containing copper derivative (II′) to compound (III). Exemplary of said copper compound are the cuprous halides (CuY; Y being halogen atom, e.g., Cl, Br, I) and lithium copper chloride (LiCuCl$_2$, Li$_2$CuCl$_4$). The reaction of the Grignard reagent and the copper compound, upon admixture, proceed smoothly to form the copper derivative (II′).

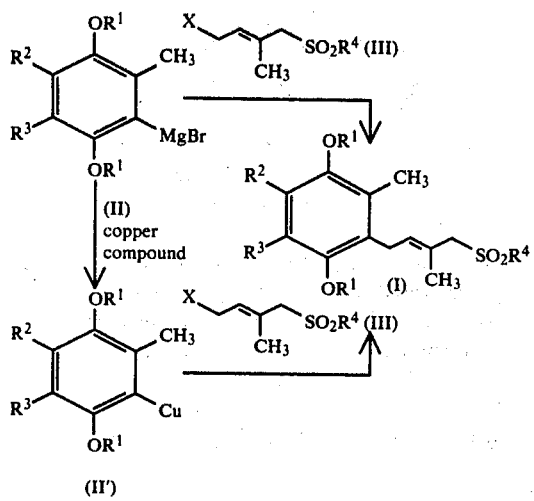

Preferably, the reaction to form the above-mentioned Grignard reagent (II) and the subsequent reaction of compound (III) with Grignard reagent (II) with the aid of a copper compound are carried out in an atmosphere of inert gas such as nitrogen, argon or helium. Solvents suitable for carrying out the reaction according to the above-mentioned process (A) or (B) are ethers, such as diethyl ether, tetrahydrofuran, dioxane and diethylene glycol dimethyl ether, aromatic hydrocarbons, such as benzene, toluene and xylene, aliphatic hydrocarbons such as hexane, heptane and octane, hexamethylphosphoric triamide, and mixtures thereof. The solvent employed need not be the same as the one used for the preparation of the Grignard reagent. The reaction can be conducted at temperatures within the range of about $-70°$ C. to about 60° C. Considering the simplicity of the operation and the selectivity of the reaction, however, temperatures between $-20°$ C. and room temperature are preferred. The reaction time is, depending upon the reaction temperature, 1 to 20 hours.

In the reaction of the Grignard reagent (II) with the compound (III) with the aid of a copper compound according to the invention, the Grignard reagent is preferably used in an amount of about 1 to about 4 moles per mole of compound (III). In the event the reaction is carried out in accordance with the above process (A), the copper compound is regenerated as the reaction proceeds, and, consequently, the amount of the copper compound to be utilized is determined, theoretically, in consideration of the rate of reaction. Generally, however, the copper compound is added in an amount, calculated in cuprous chloride equivalent, of 0.01 to 2 moles, preferably about 1 mole, per mole of compound (III). In process (A), it is desirable that the addition of the Grignard reagent (II) to a slution of a mixture of the compound (III) and the copper compound be carried out at a relatively slow rate which is comparable to the rate of conversion of the compound (II) into the compound (II') in the reaction system. In the event the reaction is conducted according to above process (B), the copper compound and Grignard reagent (II) should be employed in amounts sufficient to provide the necessary amount of copper derivative (II') which is consumed in an equimolar amount to the compound (III) through the reaction therewith.

The copper compound may be used in an amount, e.g., as little as 0.5 mole or as great as 5 moles per mole of Grignard reagent (II). Generally, however, same is employed in an amount, in terms of cuprous halide, approximately equimolar to that of Grignard reagent (II). In process (B), the addition of the copper derivative (II') to a solution of compound (III) need not be as slow as in process (A).

The $R^1$ which represents a protecting or blocking group for the hydroxyl group in the compounds of the formula (I) and of the formula (II) is lower alkyl such as methyl, ethyl, propyls, butyls or pentyls, lower alkoxy lower alkyl such as methoxymethyl, ethoxymethyl, ethoxyethyls or butoxyethyls, or methoxyethoxymethyl. Since said protecting group ultimately is to be cleaved, it is desirable that the protecting group be easily cleaved in an optional step after the preparation of the compound (I). It is further required that the protecting group be stable during the Grignard reaction and thus afford high yield resulting therefrom. Stated differently, the protecting group is required to ensure appropriate chemical stability and sufficient protection during the Grignard reaction. In this respect, the lower alkyls, lower alkoxy lower alkyls and methoxyethoxymethyl are useful protecting groups, and the methoxyethoxymethyl group is especially preferred. Benzyl and acetyl are quite unsuited as protective groups because these hydroquinone derivatives whose hydroxy groups are protected thereby are incapable of ultimately providing the corresponding Grignard reagents.

The Grignard reagents of formula (II) wherein $R^1$ is methoxyethoxymethyl are novel compounds and can be prepared, as illustrated in the following reaction sequence, by reacting the corresponding brominated hydroquinone derivative with a methoxyethoxymethyl halide in a manner knonw per se [Tetrahedron Letters, (11), 809(1976)] and then reacting the resulting methoxyethoxymethylated hydroquinone derivative (IV) with metallic magnesium in tetrahydrofuran at about 0°–60° C.:

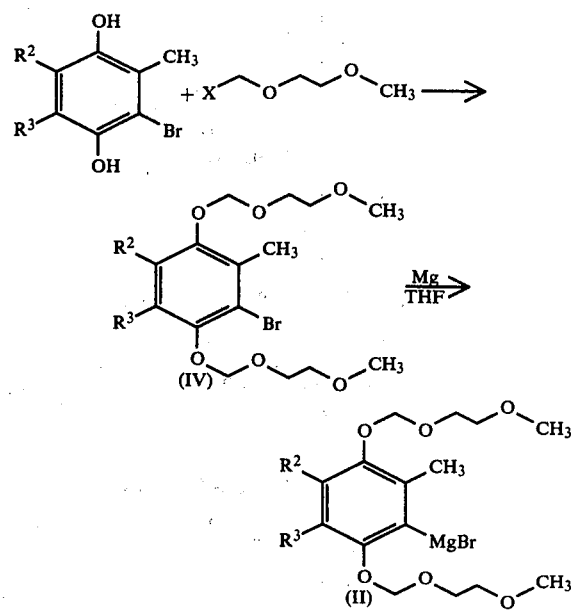

In the above equations, X is a halogen atom such as Cl, Br or I, and $R^2$ and $R^3$ are as defined above. The brominated hydroquinone derivatives of formula (IV) are also novel compounds.

Exemplary of the novel compounds (I) of the present invention, which display marked advantage in respect of yield and stereoselectivity in the production of coenzyme Q, vitamin K and other polyprenyl-trimethylquinones, are:

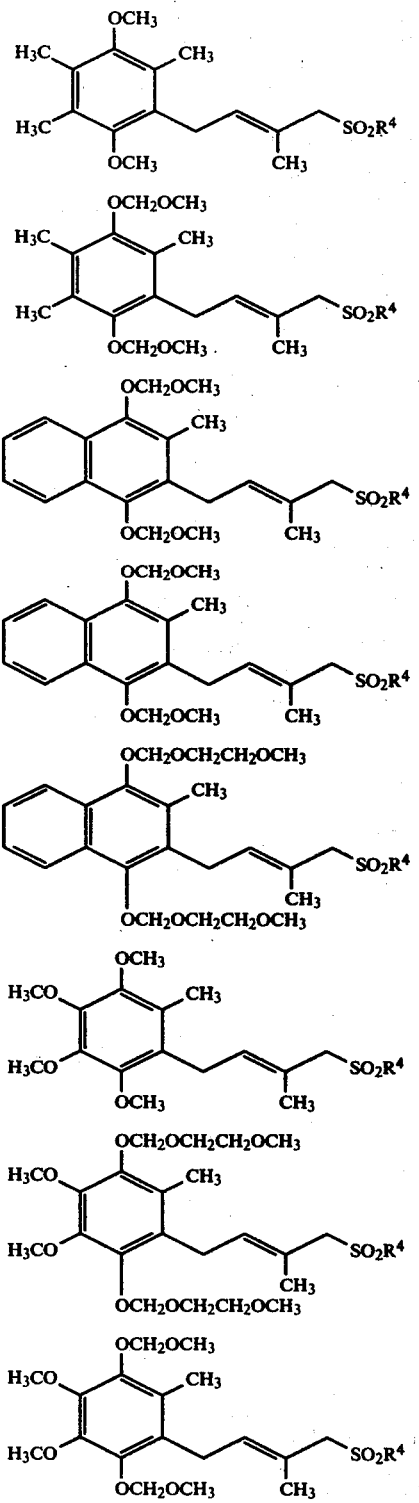

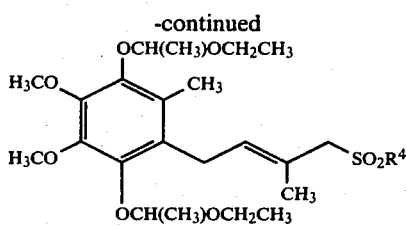

In the above formulas, $R^4$ is as defined above and represents a substituted or unsubstituted aromatic hydrocarbon residue having from 6 to 10 nuclear carbons, for example phenyl, lower alkyl-substituted phenyl such as tolyl and xylyl or naphthyl. From the aforesaid compounds, the aforementioned quinones which are useful medicinals are derived, according to the following sequence of steps:

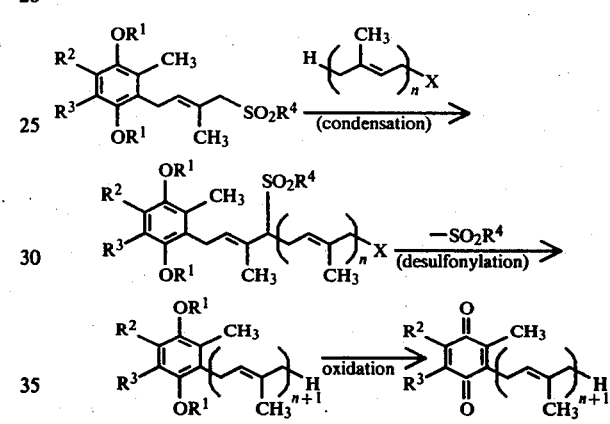

In the above equations, n is an integer of from 1 to 11, $R^1$, $R^2$, $R^3$, $R^4$ and X are as defined above. The condensation reaction of the compound (I) of the invention with the polyprenyl halide is carried out in the presence of a basic compound in an amount of about 1–2 moles per mole of compound (I), at a temperature within the range between such a low temperature as −78° C. and room temperature, under an inert gas atmosphere. Examples of such basic compound are organic lithium compounds such as n-butyllithium, methyllithium and phenyllithium, Grignard reagents such as ethylmagnesium bromide and phenylmagnesium bromide, alkali metal amides such as diisopropyl lithium amide, lithium amide and sodium amide, and alkali metal alkoxides. The elimination of the sulfonyl moiety is effected in conventional manner by reacting the condensation product with an alkali metal such as lithium, sodium or potassium, in a lower alkylamine, such as methylamine, ethylamine or diethylamine, or ammonia, as solvent, preferably at a temperature of −78° C. to 0° C. In those cases where the protecting group $R^1$ is not removed by the above oxidation reaction, any appropriate reaction for elimination of the protecting group, such as hydrolysis, is conducted prior to the oxidation reaction.

In order to further illustrate the present invention and the advantages thereof, the following specific examples are given, it being understood that same are intended only as ilustrative, and in no way limitative.

REFERENCE EXAMPLE 1

Preparation of bromotrimethylhydroquinone dimethyl ether

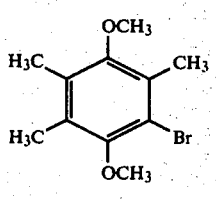

First, according to the method of L. I. Smith et al. [*J. Am. Chem. Soc.*, 64, 440 (1942)], 420 g of trimethylquinone were dissolved in 4 liters of carbon tetrachloride, then 448 g of bromine were added dropwise thereto at room temperature over a period of 3 hours, and, thereafter, the mixture was stirred for one hour. The reaction mixture was thence treated with an aqueous saturated solution of sodium hydrogen carbonate, and then washed with water. The resulting crystalline precipitate was filtered off and the filtrate was dried. The mother liquor was concentrated under reduced pressure to form black-colored crystals which were then dissolved in hot ethanol, and solid sodium hydrogen carbonate was added to the ethanolic solution until the evolution of carbon dioxide gas ceased. Nitric acid was then added portionwise, and, after a change in color of the solution from red to yellow, the solution was cooled and the resulting crystals were recovered. The mother liquor was concentrated to obtain additional crystals. The crystals were collected and recrystallized from hot ethanol providing 475 g (75% yield) of the bromoquinone. The thus obtained bromoquinone was next suspended in 3 liters of acetic acid plus 2 liters of water, 280 g of zinc were added, and the mixture was heated, first at 80°–90° C. for 2 hours, and then under reflux for an additional two hours. The unreacted zinc was separated by decantation, and the reaction mixture was poured into water. There were obtained 383 g (80% yield) of trimethylbromohydroquinone as white crystals.

Into 1060 ml of dimethyl sulfuric acid, 188 g of the above bromohydroquinone were suspended, and a solution of 1700 mg of potassium hydroxide in 3400 ml of water was added thereto portionwise at about 10° C., in a nitrogen atmosphere. After completion of the addition, the temperature of the reaction mixture was raised to 50°–60° C., and the mixture was stirred for one hour. The mixture was then poured into water and extracted with ether. The ether layer was washed with an aqueous 5% sodium hydroxide solution and then with water, dried, and concentrated. The resulting crystalline precipitate was recrystallized from methanol, to provide 130 g (62% yield) of bromotrimethylhydroquinone dimethyl ether.

REFERENCE EXAMPLE 2

Preparation of bromomethylnaphthohydroquinone dimethyl ether

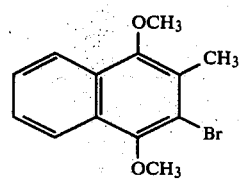

The method of R. Adams et al. [*J. Am. Chem. Soc.*, 63, 528 (1941)] was employed. Thus, a mixture of 200 g of 2-methyl-naphthoquinone, 400 g of dried sodium acetate and 1800 ml of acetic acid was heated to 50° C., 204 g of bromine were added dropwise thereto, and the mixture was stirred at the same temperature for 18 hours. The reaction mixture was poured into 4 liters of water, and the crystals which precipitated on cooling were filtered off and recrystallized from methanol, giving 225 g of the yellowish bromoquinone.

To 1750 ml of 85% ethanol were added 130 g of the above bromoquinone, then a solution of 360 g of stannous chloride in 360 ml of concentrated hydrochloric acid was added under ice cooling, and the mixture was stirred at the same temperature for 4 hours. The reaction was carried out in a nitrogen atmosphere. Water (1700 ml) was added to the reaction mixture, the resulting crystals were redissolved by heating, the solution was allowed to stand, and the resulting white crystals (114 g, 87% yield) were collected.

Into 530 ml of dimethyl sulfuric acid were suspended 103 g of the obtained bromohydroquinone, and potassium hydroxide (846 g)/water (1700 ml) was added portionwise under ice cooling in a nitrogen atmosphere. After such addition, the reaction temperature was raised to 50°–60° C., and then the mixture was stirred for one hour. The reaction mixture was poured into water and extracted with ether. The ether layer was washed with an aqueous 5% sodium hydroxide solution and then with water, dried and concentrated. The crystals thus obtained were recrystallized from methanol to give 79 g (69.3% yield) of bromomethylnaphthohydroquinone dimethyl ether.

EXAMPLE 1

A Grignard reagent was prepared by reacting 12.96 g (50 mmol) of the bromotrimethylhydroquinone dimethyl ether prepared in Reference Example 1 with 1.44 g of magnesium in tetrahydrofuran (THF) in the presence of a small amount of ethyl bromide, at room temperature.

The above Grignard reagent (solution in 150 ml of THF) was added dropwise to a suspension of 6.1 g (25 mmol) of 1-(benzenesulfonyl)-2-methyl-4-chloro-2-butene (trans isomer) and 4.1 g of cuprous bromide in 50 ml of THF at −10° to 0° C. over a period of about 2 hours. After such dropwise addition, stirring was carried out for an additional 2 hours to complete the reaction. The reaction mixture was poured into water, neutralized with 3 g of acetic acid in 20 ml of water, and extracted with chloroform. The extract was washed with water, and dried, and then the chloroform solvent was evaporated therefrom. Methanol (200 ml) was added to the residue, and the crystals which precipitated were recovered. The mother liquor was concentrated to recover a second crop of crystals. The yield of the thus produced 2,3,5-trimethyl-5-(3'-methyl-4'-benzenesulfonyl-2'-buten-1'-yl)-hydroquinone dimethyl ether occurring as white crystals, and having a melting point of 127°–129° C., was 66.7 g (68.5% yield). The structure was confirmed by the following data:

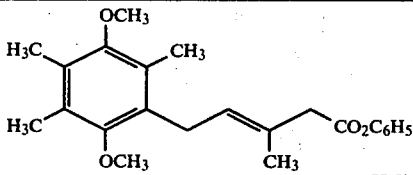

Nuclear magnetic resonance spectrum ($\delta_{ppm}$ in $CDCl_3$)

| | |
|---|---|
| 1.90 | s, 3H, $CH_3$ |
| 1.96, 2.13 | s, 9H, $CH_3$ |
| 3.27 | d, 2H, $-CH_2-$, J=7Hz |
| 3.50, 3.58 | s, 6H, $-OCH_3$ |
| 3.66 | s, 2H, $-CH_2-$ |
| 4.93 | t, 1H, $=CH-$, J=7Hz |
| ca. 7.20–7.80 | m, 5H, arom H |

EXAMPLE 2

A Grignard reagent was prepared by reacting, as in Example 1, the bromomethylnaphthohydroquinone dimethyl ether prepared by the procedure of Reference Example 2 with magnesium in the presence of a small amount of ethyl bromide in THF.

The above Grignard reagent (16 mmol/40 ml THF solution) was added dropwise at 0° C. over a period of one hour to a solution of 1.7 g (7 mmol) of 1-benzenesulfonyl)-2-methyl-4-chloro-2-butene (trans isomer) in 10 ml of THF in which an equimolar amount of cuprous bromide had been suspended. Then the reaction temperature was raised to room temperature, and stirring was carried out for 3 hours. The reaction mixture was poured into ice water, acidified with acetic acid, and extracted with chloroform. The chloroform layer was washed with water, dried and concentrated. Methanol was added to the residue and the resulting crystalline precipitate was recovered. Concentration of the mother liquor, followed by the same procedure, provided another crop of crystals. The yield of the product thus obtained and occurring as white crystals, and having a melting point of 156°–157° C., was 70.4%. The structure was confirmed by the following data:

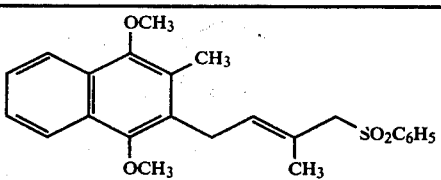

Nuclear magnetic resonance spectrum ($\delta_{ppm}$ in $CDCl_3$)

| | |
|---|---|
| 1.93 | s, 3H, $CH_3$ |
| 2.13 | s, 3H, $CH_3$ |
| 3.40 | d, 2H, $CH_2$, J=7Hz |
| 3.65, 3.72, 3.78 | s, 8H, $CH_3O-$, $CH_2$ |
| 4.96 | t, 1H, $=CH-$, J=7Hz |
| ca. 7.18–8.05 | m, 5H, arom H |

EXAMPLES 3–15

The Grignard reagent [noted as (II) in the Table which follows], prepared in the same manner as in Example 2 and the compound (trans isomer) represented by the following structural formula [noted as (III)]:

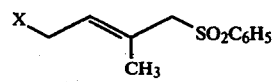

were reacted in the same manner as in Example 2, except that (a) compound (III) was added dropwise to a solution of a mixture of Grignard reagent (II) and the copper compound, or (b) Grignard reagent was added dropwise to a solution of a mixture of compound (III) and the copper compound; there was obtained the same product [noted as (I)] as in Example 2. The results are summarized in the Table:

TABLE

| Ex. | Amount of (II) | (III) X | (III) Amount | Cu compound Kind | Cu compound Molar ratio to (II) | Solvent | Reaction conditions | Yield of (I) (%) |
|---|---|---|---|---|---|---|---|---|
| 3 | 8 mmol (THF 20 ml) | Cl | 7 mmol (THF 10 ml) | CuI | 1/4 | THF | (III) added dropwise at −20° C. (over 30 minutes); −20° C. 2 hours; room temp. 15 hours | ca. 5 |
| 4 | 8 mmol (THF 20 ml) | " | 7 mmol (THF 10 ml) | " | 1/1 | " | (III) added dropwise at −20° C. (over 30 minutes); −20° C. 2 hours; room temp. 15 hours | 24.4 |
| 5 | 8 mmol (THF 20 ml) | " | 7 mmol (THF 10 ml) | CuCl | " | " | (III) added dropwise at −40° C. (over 30 mins); −40° C. 3 hours; room temp. 15 hours | 16.0 |
| 6 | 8 mmol (THF 20 ml) | " | 7 mmol (THF 10 ml) | CuBr | " | " | (III) added dropwise at −40° C. (over 30 mins); −40° C. 3 hours; room temp. 15 hours | 26.1 |
| 7 | 8 mmol (THF 20 ml) | " | 7 mmol (THF 10 ml) | CuCl | " | " | (III) added dropwise at −60° C. (over 5 mins.); −60° C. 3 hours; room temp. 30 minutes | 34.4 |
| 8 | 8 mmol (THF 20 ml) | " | 7 mmol (THF 10 ml) | CuBr | " | " | (III) added dropwise at −60° C. (over 5 mins.); −60° C. 3 | 28.6 |

TABLE-continued

| Ex. | Amount of (II) | (III) X | Amount | Cu compound Kind | Molar ratio to (II) | Solvent | Reaction conditions | Yield of (I) (%) |
|---|---|---|---|---|---|---|---|---|
| 9 | 8 mmol (THF 20 ml) | " | 7 mmol (THF 10 ml) | " | " | " | hours; room temp. 30 minutes (II) added dropwise at 0° C. (over 30 minutes); 0° C., 2 hours | 41.1 |
| 10 | 8 mmol (THF 20 ml) | " | 7 mmol (THF/ hexane 1/1) | " | " | THF/ hexane 1/1 | (II) added dropwise at 0° C. (over 30 minutes); 0° C. 2hrs. | 40.4 |
| 11 | 8 mmol (THF 20 ml) | " | 7 mmol (THF 10 ml) | " | " | THF | (II) added dropwise at 0° C. (over 30 mins) room temp. 6 hrs. | 44.0 |
| 12 | 8 mmol (THF 20 ml) | Tosyl | 7 mmol (THF 10 ml) | " | " | " | (II) added dropwise at 0° C. (over 30 mins) room temp. 6 hrs. | 35.2 |
| 13 | 8 mmol (THF 20 ml) | Cl | 7 mmol (THF 10 ml) | " | " | " | (II) added dropwise at room temp. (over 30 mins.); room temp. 6hrs. | 34.1 |
| 14 | 8 mmol (THF 20 ml) | " | 7 mmol (THF 10 ml) | " | " | " | (II) added dropwise at −30° C. (over 30 mins.) room temp. 2 hrs. | 23.3 |
| 15 | 28 mmol (THF 70 ml) | " | 7 mmol (THF 10 ml) | " | " | " | (II) added dropwise at 0° C. (over 2 hrs.) room temp. 3 hrs. | 67.0 |

EXAMPLE 16

Reaction of 31.9 g (100 mmol) of bromotrimethylhydroquinone dimethoxymethyl ether with 2.64 g of magnesium in the presence of a small amount of ethyl bromide in THF, at room temperature, provided the Grignard reagent of said hydroquinone derivative.

The above Grignard reagent (solution in 200 ml of THF) was added dropwise at −10° C. to 0° C. over a period of about 3 hours to a suspension of 11.2 g (46 mmol) of 1-(benzenesulfonyl)-2-methyl-4-chloro-2-butene (trans isomer) and 7.54 g of cuprous bromide in 300 ml of THF. After such dropwise addition, stirring was carried out for an additional 2 hours. The reaction mixture was poured into water, neutralized with a solution of 6 g of acetic acid in 40 ml of water, and extracted with chloroform. Washing with water, drying and evaporation of the chloroform were followed by the addition of 200 ml of methanol to the residue. The resulting crystals were collected (8.46 g). Concentration of the mother liquor provided another crop of crystals. The yield of the product thus obtained, and having a melting point of 98°-99° C., was 11.58 g (56.2% yield). The structure was confirmed by the following data:

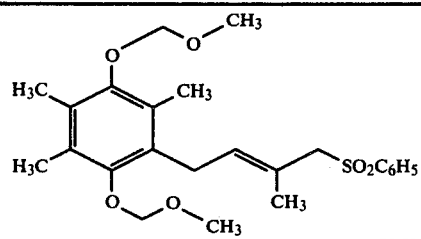

Nuclear magnetic resonance spectrum ($\delta_{ppm}^{in\ CDCl_3}$)

| | |
|---|---|
| 1.87 | s, 3H, CH$_3$ |
| 1.96, 2.10, 2.12 | s, 9H, CH$_3$ |

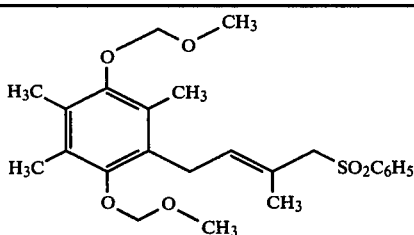

Nuclear magnetic resonance spectrum ($\delta_{ppm}^{in\ CDCl_3}$)

| | |
|---|---|
| 3.27 | d, 2H, CH$_2$, J=7Hz |
| 3.46, 3.53, 3.63 | s, 8H, CH$_3$O—, —CH$_2$— |
| 4.77, 4.78 | s, 4H, —OCH$_2$— |
| 4.93 | t, 1H, =CH, J=7Hz |
| ca. 7.20–7.80 | m, 5H, arom H |

EXAMPLE 17

Reaction of 20.64 g (60 mmol) of bromomethylnaphthohydroquinone with 1.73 g of magnesium in the presence of a small amount of ethyl bromide in THF at room temperature provided the Grignard reagent of said hydroquinone derivative.

The above Grignard reagent was added dropwise at 0° C. over a period of 3 hours to a suspension of 7.32 g (30 mmol) of 1-(benzenesulfonyl)-2-methyl-4-chloro-2-butene (trans isomer) and 4.93 g of cuprous bromide in 100 ml of THF. After such dropwise addition, the reaction was continued at the same temperature for an additional 2 hours. The reaction mixture was poured into water, neutralized with a solution of 4.0 g of acetic acid in 40 ml of water, and extracted with chloroform. The chloroform extract was washed with water, dried and evaporated. Methanol (200 ml) was added to the residue to effect precipitation of crystals at 0° C. The product thus obtained as a white crystalline substance had a melting point of 73°–75° C. and weighed 10.2 g (72% yield). The structure was confirmed by the following data:

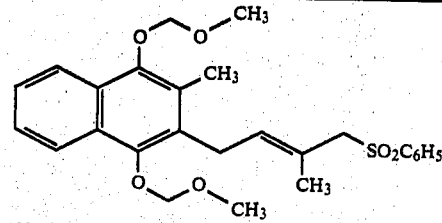

| Nuclear magnetic resonance spectrum ($\delta_{ppm}$ in $CDCl_3$) | |
|---|---|
| 1.90 | s, 3H, $CH_3$ |
| 2.16 | s, 3H, $CH_3$ |
| 3.53, 3.60 | s, 6H, $CH_3O$— |
| ca. 3.40–3.63 | m, 4H, —$CH_2$—, —$CH_2SO_2$— |
| 4.91, 5.00 | s, 4H, —$CH_2O$— |
| ca. 4.90–5.10 | (t), 1H, =CH— |
| 7.18–8.03 | m, 9H, arom H |

REFERENCE EXAMPLE 3

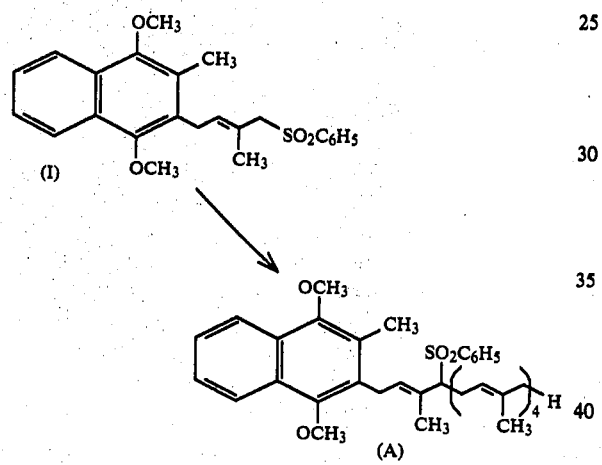

A 15% hexane solution (4.34 ml) of n-butyllithium was added dropwise at −60° C. to a solution of 2.05 g (5 mmol) of the hydroquinone derivative (I) produced by the procedure of Example 2 in a mixed solvent consisting of THF and hexamethylphosphoric triamide (3:1), and the mixture was stirred at the same temperature for 10 minutes. Then 1.95 g (5.5 mmol) of all-trans geranylgeranyl bromide was added to the above solution at −60° C. After stirring at the same temperature for 30 minutes, the temperature was raised to room temperature and the reaction was continued at room temperature for 2 hours. The reaction mixture was poured into water, acidified with acetic acid, and extracted with isopropyl ether. The crude product weighed 3.70 g and was purified by silica gel column chromatography (isopropyl ether/n-hexane=3/7), providing 2.51 g (73% yield) of the purified pale-yellow liquid condensation product represented by the aforesaid structural formula (A). The structure was confirmed by the following data:

| Nuclear magnetic resonance spectrum ($\delta_{ppm}$ in $CDCl_3$) | |
|---|---|
| 1.53, 1.60 | s, 15H, $CH_3$ |
| 1.93 | s, 3H, $CH_3$ |
| 2.10 | s, 3H, $CH_3$ |
| ca. 1.83–2.10 | m, 12H, —$CH_2CH_2$— |
| ca. 2.30–2.90 | m, 2H, —$CH_2$— |
| 3.36 | d, 2H, —$CH_2$—, J=7Hz |
| ca. 3.33–3.54 | m, 1H, —$\overset{|}{C}H$—$SO_2$— |
| 3.67, 3.78 | s, 6H, $CH_3O$— |
| 4.77–5.13 | m, 5H, =CH— |
| ca. 7.20–8.10 | m, 5H, arom. H |

EXAMPLE 18

A Grignard reagent was prepared by reacting 14.5 g (50 mmol) of 2,3,4,5-tetramethoxy-6-methyl-1-bromobenzene with 1.6 g (66 mmol) of metallic magnesium, in 120 ml of tetrahydrofuran.

The above Grignard reagent was added dropwise at 0° C. over a period of 2 hours to a suspension of 6.1 g (25 mmol) of 1-benzenesulfonyl)-2-methyl-4-chloro-2-butene (trans isomer) and 7.1 g (50 mmol) of cuprous bromide in 100 ml of tetrahydrofuran. After such dropwise addition, stirring was continued at the same temperature for 2 hours to complete the reaction. The reaction mixture was poured into ice water, acidified with acetic acid, and extracted with chloroform. The chloroform layer was washed with water and dried. The solvent was distilled off from the chloroform solution under reduced pressure, and the residue (17.8 g) was purified by silica gel chromatography (developing solvent: chloroform). There were obtained 8.5 g of 2,3,4,5-tetramethoxy-6-methylbenzene as fastest moving component fraction and 8.7 g (80% yield) of the subject compound as later recovered eluate. The subject compound was recovered as a liquid, and, then permitted to stand for a long period of time, same solidified (the crude product had a melting point of 71°–75° C.). The structure was confirmed as follows:

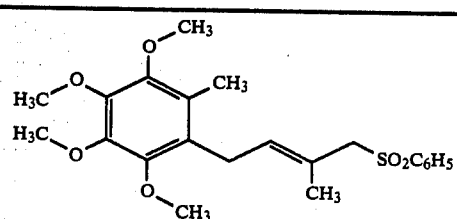

| Nuclear magnetic resonance spectrum ($\delta_{ppm}$ in $CDCl_3$) | |
|---|---|
| 1.85 | s, 3H, $CH_3$ |
| 1.90 | s, 3H, $CH_3$ |
| 3.15 | d, 2H, —$CH_2$—, J = 7Hz |
| 3.63, 3.70, 3.80, 3.83 | s, 12H, $CH_3O$— |
| ca. 3.60–3.9: | Indistinct due to overlapping with the $CH_3O$— peaks. However, integration has affirmed that the two protons of —$CH_2SO_2$— are involved. |
| 4.85 | t, 1H, =CH—, J = 7Hz |
| 7.20–7.75 | m, 5H, arom. H |

EXAMPLE 19

A Grignard reagent was prepared by reacting 10.20 g (29 mmol) of 2,3-dimethoxy-5-methyl-6-bromobenzohydroquinone di-methoxymethyl ether with 0.8 g (33 mmol) of metallic magnesium in 100 ml of tetrahydrofuran.

The above Grignard reagent was added dropwise at 0° C. over a period of 2 hours to a suspension of 4.88 g (20 mmol) of 1-(benzenesulfonyl)-2-methyl-4-chloro-2-butene (trans isomer) and 4.26 g (30 mmol) of cuprous bromide in 100 ml of tetrahydrofuran. After such dropwise addition, the reaction was continued at the same temperature for 2 hours. The reaction mixture was poured into ice water, neutralized with acetic acid, and extracted with chloroform. The chloroform layer was washed with water, and dried. The solvent was distilled off from the chloroform layer under reduced pressure, and the residue was subjected to purification by silica gel column chromatography (developing solvent: chloroform), to provide 6.9 g (72% yield) of the subject product as viscous liquid. The structure was confirmed by the following data:

Nuclear magnetic resonance spectrum ($\delta_{ppm}$ in $CDCl_3$)

| | |
|---|---|
| 1.87 | s, 3H, $CH_3$ |
| 1.97 | s, 3H, $CH_3$ |
| 3.23 | d, 2H, $-CH_2-$, J = 7Hz |
| 3.45, 3.53, 3.76, 3.80 | s, 12H, $CH_3O-$ |
| 3.65 | s, 2H, $-CH_2SO_2-$ |
| 4.90, 4.97 | s, 4H, $-OCH_2O-$ |
| ca. 4.80–5.10 | m, 1H, $=CH-$ |
| 7.20–7.80 | m, 5H, arom. H |

REFERENCE EXAMPLE 4

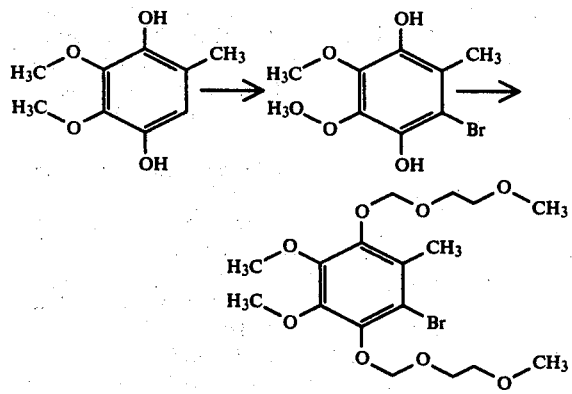

(1) 2,3-Dimethoxy-5-methyl-6-bromohydroquinone

A solution of 39.5 g of bromine in 70 ml of chloroform was added dropwise at about 5° C. to a solution of 46.0 g of 2,3-dimethoxy-5-methylhydroquinone in 500 ml of chloroform, under a nitrogen atmosphere. Stirring was continued at the same temperature for 3 hours, and then the reaction mixture was washed with water until the washings were colorless. The organic layer was dried over magnesium sulfate, and the solvent was distilled off under reduced pressure to provide 65.5 g of 2,3-dimethoxy-5-methyl-6-bromohydroquinone.

(2) Methoxyethoxymethyl chloride

Hydrogen chloride gas was bubbled through an ice-cooled mixture of 152 g of methyl cellosolve and 66 g of s-trioxane until a transparent solution resulted. Extraction with pentane, drying of the pentane solution over magnesium sulfate, removal of the solvent by distillation under reduced pressure and further distillation under reduced pressure gave methoxyethoxymethyl chloride (boiling point: 82° C./75 mm Hg). This synthesis was performed essentially in accordance with the method described in Tetrahedron Letters, (11), 809 (1976).

(3) 2,3-Dimethoxy-5-methyl-6-bromohydroquinone 1,4-dimethoxyethoxymethyl ether

Fifty percent sodium hydride (22.9 g) was added portionwise to a cooled solution (−30° C.) of 62.5 g of 2,3-dimethoxy-5-methyl-6-bromohydroquinone in 880 ml of dimethylformamide. After such addition, the mixture was stirred at the same temperature for one hour, and thereafter 65 g of methoxyethoxymethyl chloride was added dropwise at −30° C. After such dropwise addition, stirring was continued for 3 hours, then 50 ml of ethanol was added, and the entire mixture was stirred for one hour. The reaction mixture was poured into ice water, and extracted with isopropyl ether. The organic layer was dried over magnesium sulfate and dried, and the solvent was distilled off under reduced pressure. Thus were obtained 91.5 g (88% yield) of 2,3-dimethoxy-5-methyl-6-bromohydroquinone 1,4-dimethoxyethoxymethyl ether. This product was identified by the following data:

Infrared absorption spectrum (neat): 2930, 2875, 1458, 1410, 1386, 1340, 1238, 1166, 1115, 1078, 966 cm$^{-1}$.

Nuclear magnetic resonance spectrum ($CDCl_3$): $\delta = 5.12$ (d, 4H), 4.05–3.78 (m, 4H), 3.80 (s, 6H), 3.60–3.43 (m, 4H).

EXAMPLE 20

A Grignard reagent was prepared in conventional manner by reacting 32.4 g (74 mmol) of 2,3-dimethoxy-5-methyl-6-bromohydroquinone 1,4-dimethoxyethoxymethyl ether prepared by the procedure of Reference Example 4 with 1.8 g of metallic magnesium in 500 ml of dried tetrahydrofuran. To the tetrahydrofuran solution of the Grignard reagent were added 10.6 g of cuprous bromide, and the mixture was stirred at room temperature for one hour. The resulting solution was added dropwise with ice cooling to a solution of 11.8 g (50 mmol) of 1-(benzenesulfonyl)-2-methyl-4-chloro-2-butene (trans isomer) in 200 ml of tetrahydrofuran. After such dropwise addition, the mixture was stirred at room temperature for 3 hours, poured into water, acidified with dilute hydrochloric acid, and extracted with ether. The ether layer was washed with water and dried, and the solvent was distilled off under reduced pressure. The residue was purified by silica gel column chromatography with a dioxane/hexane (3/7) mixture as developing solvent, to provide 24.04 g (85.7% yield) of 2,3-dimethoxy-5-methyl-6-(3′-methyl-4′-benzenesulfonyl-2′-buten-1′-yl)hydroquinone dimethoxyethoxymethyl ether as viscous pale-yellow liquid. The structure of the product was confirmed by the following data:

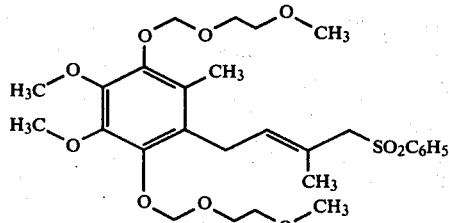

Nuclear magnetic resonance spectrum ($\delta_{ppm}$ in CDCl$_3$)

| 1.87 | s, 3H, CH$_3$ |
|---|---|
| 1.97 | s, 3H, CH$_3$ |
| ca. 3.03–4.00 | m, 24H, —CH$_2$CH$_2$—, —OCH$_3$, —CH$_2$—C=, —CH$_2$SO$_2$— |
| 4.00, 4.07 | each s, 4H, —OCH$_2$O— |
| ca. 4.90–5.20 | m, 1H, =CH— |
| ca. 7.23–7.80 | m, 5H, arom. protons |

Infrared absorption spectrum (neat)
1580, 1460, 1305, 1160, 1130, 1020, 970 cm$^{-1}$

EXAMPLE 21

The solution of the Grignard reagent prepared by the procedure of Example 20 was added dropwise at 0° C. over a period of 2 hours to a suspension of 11.8 g of 1-(benzenesulfonyl)-2-methyl-4-chloro-2-butene (trans isomer) and 10.6 g of cuprous bromide in 100 ml of tetrahydrofuran. The resulting mixture was stirred at room temperature for 3 hours, and then subjected to the same treatment as in Example 20, to provide 20.92 g (74.6% yield) of 2,3-dimethoxy-5-methyl-6-(3'-methyl-4'-benzenesulfonyl-2'-buten-1'-yl)hydroquinone dimethoxyethoxymethyl ether.

REFERENCE EXAMPLE 5

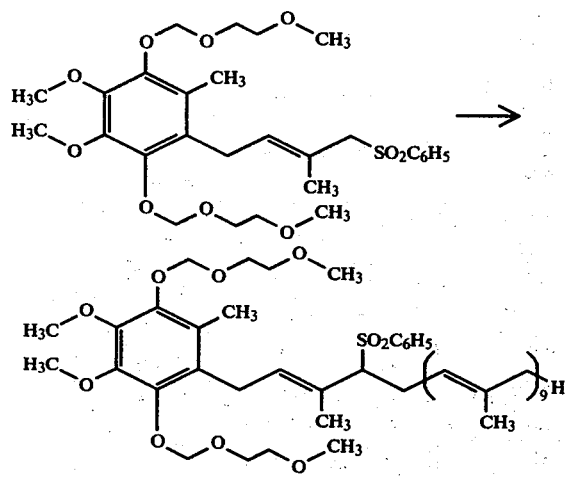

Into 230 ml of a mixed solvent consisting of tetrahydrofuran and hexamethylphosphoric triamide (3/1 by volume), there were dissolved 20.5 g (36 mmol) of the condensation product obtained in Example 20. To this solution were added dropwise, at about −50° C., 36.2 ml of a 15% n-butyllithium solution in hexane. After such addition, stirring was continued at the same temperature for about one hour. To the solution which had turned red and transparent, there was added dropwise at −50° to −40° C. a solution of 30.09 g of solanesyl bromide in 50 ml of hexane/tetrahydrofuran (1/1 by volume). After such dropwise addition, the mixture was stirred at the same temperature for 30 minutes, and thereafter the reaction temperature was raised to room temperature and the reaction was continued for 5 hours. The progress of the reaction was followed by thin layer chromatography (developing solvent: dioxane/hexane=3/7; R$_f$ of the starting material≈0.2, R$_f$ of the subject compound=0.55). The reaction mixture was poured into water weakly acidified with dilute hydrochloric acid, and extracted with isopropyl ether. The extract layer was washed with water, and dried. The solvent was distilled off from the thus obtained isopropyl ether solution by reduced pressure distillation, and the residue (46.62 g) was purified by silica gel chromatography (developing solvent: dioxane/hexane 3/7), providing 38.84 g (91.2% yield) of the reaction product depicted by the above formula.

Infrared absorption spectrum of the product (neat): 1660, 1450, 1300, 1250, 1340, 1320, 975 and 875 cm$^{-1}$.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A hydroquinone compound having the structural formula:

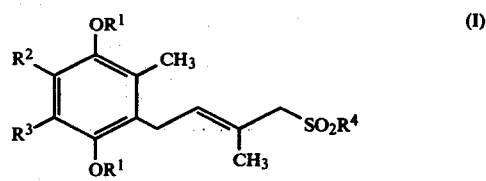

wherein R$^1$ is methoxyethoxymethyl, R$^2$ and R$^3$ are each selected from the group consisting of methyl and methoxy, and R$^2$ and R$^3$, taken together with the carbon atoms from which they depend, can form a benzene ring, and R$^4$ is a lower alkyl substituted or unsubstituted aromatic hydrocarbon having from 6 to 10 nuclear carbons.

2. The hydroquinone compound as defined by claim 1, wherein R$^2$ and R$^3$ are each methyl.

3. The hydroquinone compound as defined by claim 1, wherein R$^2$ and R$^3$ are each methoxy.

4. The hydroquinone compound as defined by claim 1, wherein R$^2$ and R$^3$, taken together with the carbon atoms from which they depend, define a benzene ring.

5. The hydroquinone compound as defined by any of claims 1, 2, 3 or 4, wherein R$^4$ is selected from the group consisting of phenyl, lower alkyl-substituted phenyl and naphthyl.

6. A process for preparation of the hydroquinone compound having the structural formula:

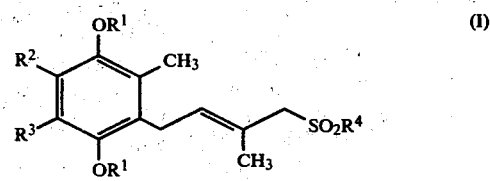

wherein $R^1$ is selected from the group consisting of lower alkyl, lower alkoxy lower alkyl and methoxyethoxymethyl, $R^2$ and $R^3$ are each selected from the group consisting of methyl and methoxy, and $R^2$ and $R^3$, taken together with the carbon atoms from which they depend, can form a benzene ring, and $R^4$ is a lower alkyl substituted or unsubstituted aromatic hydrocarbon having from 6 to 10 nuclear carbons comprising reacting a compound having the structural formula:

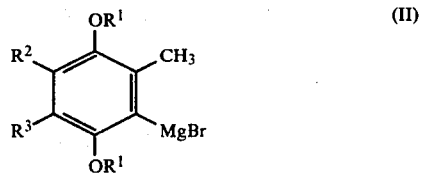
(II)

wherein $R^1$, $R^2$ and $R^3$ are as defined above, with a compound having the structural formula:

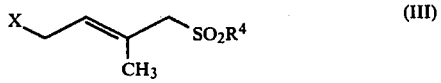
(III)

wherein X is selected from the group consisting of halogen and tosyl, with the aid of a copper compound selected from the group consisting of cuprous halides and lithium copper chloride whereby said reacting comprises reacting said compound (II) with compound (III) in the presence of the copper compound, or reacting said compound (II) initially with the copper compound and the resulting reaction product therefrom being reacted with compound (III).

7. The process as defined by claim 6, wherein said cuprous halide is selected from the group consisting of cuprous chloride, cuprous bromide and cuprous iodide.

8. The process as defined by claim 6, wherein said copper compound is lithium copper chloride.

9. The process as defined by claim 6, wherein said reaction is carried out in the presence of the copper compound.

10. The process as defined by claim 9, wherein about 1 to 4 moles of compound (II) is present in the reaction mixture per mole of compound (III), and 0.01 to 2 moles of the copper compound is present per mole of compound (III).

11. The process as defined by claim 9, wherein said reaction is conducted by adding the compound (II) to a solution of a mixture of the compound (III) and said copper compound.

12. The process as defined by claim 6, wherein the compound (III) is reacted with a compound having the structural formula:

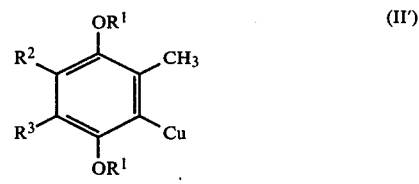
(II′)

wherein $R^1$, $R^2$ and $R^3$ are as defined in claim 6, and itself produced by reacting the compound (II) with said copper compound.

13. The process as defined by claim 12, wherein the reaction is conducted by mixing compound (II) with said copper compound and thence adding the resulting reaction mixture containing compound (II′) to compound (III).

14. A hydroquinone compound having the structural formula:

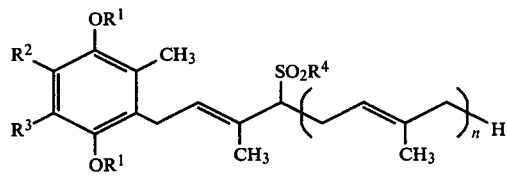

wherein $R^1$, $R^2$, $R^3$ and $R^4$ are as defined in claim 1 and n is an integer of 1 to 11.

15. The process as defined by claim 6 wherein $R^1$ is methoxyethoxymethyl.

* * * * *